(12) United States Patent
Oepen

(10) Patent No.: US 7,527,606 B2
(45) Date of Patent: May 5, 2009

(54) CATHETER HAVING MAIN BODY PORTION WITH COIL-DEFINED GUIDEWIRE PASSAGE

(75) Inventor: Randolf Von Oepen, Los Altos Hills, CA (US)

(73) Assignee: Abbott Laboratories, Abbott Park, IL (US)

( * ) Notice: Subject to any disclaimer, the term of this patent is extended or adjusted under 35 U.S.C. 154(b) by 532 days.

(21) Appl. No.: 11/136,251

(22) Filed: May 23, 2005

(65) Prior Publication Data

US 2005/0267442 A1 Dec. 1, 2005

Related U.S. Application Data

(60) Provisional application No. 60/575,643, filed on May 27, 2004.

(51) Int. Cl.
*A61M 31/00* (2006.01)
(52) U.S. Cl. .................................. 604/103.04
(58) Field of Classification Search ............. 604/103.4, 604/509, 528, 103.09
See application file for complete search history.

(56) References Cited

U.S. PATENT DOCUMENTS

| | | | |
|---|---|---|---|
| 4,490,421 A | 12/1984 | Levy | |
| 4,563,181 A | 1/1986 | Wijayarathna et al. | |
| 4,748,982 A | 6/1988 | Horzewski et al. | |
| 4,762,129 A | 8/1988 | Bonzel | |
| 4,771,777 A | 9/1988 | Horzewski et al. | |
| RE32,983 E | 7/1989 | Levy | |
| 4,877,031 A | 10/1989 | Conway et al. | |
| 4,898,591 A | 2/1990 | Jang et al. | |
| 4,921,483 A | 5/1990 | Wijay et al. | |
| 4,944,745 A | 7/1990 | Sogard et al. | |
| RE33,561 E | 3/1991 | Levy | |
| 5,047,045 A | 9/1991 | Arney et al. | |
| 5,078,702 A | 1/1992 | Pomeranz | |
| 5,102,403 A | 4/1992 | Alt | |
| 5,135,535 A | 8/1992 | Kramer | |
| 5,154,725 A | 10/1992 | Leopold | |
| 5,195,978 A | 3/1993 | Schiffer | |

(Continued)

FOREIGN PATENT DOCUMENTS

DE 197 29 499 A1 1/1999

(Continued)

*Primary Examiner*—Nicholas D Lucchesi
*Assistant Examiner*—Aarti Bhatia
(74) *Attorney, Agent, or Firm*—Baker Botts L.L.P.

(57) ABSTRACT

The invention includes a catheter having an elongate main body portion and a distal body portion. The elongate main body portion has a proximal end and a distal end. The main body portion further includes a coil having at least one complete turn about a central axis, the coil defining a passage along the central axis. The elongate distal body portion extends from the distal end of the main body portion. In accordance with a further aspect of the invention, the distal body portion has a proximal end and a distal end and can include a guidewire lumen defined along at least a portion of a length between the distal end and the proximal end of the distal body portion. The guidewire lumen has a distal guidewire port and a proximal guidewire port defined in communication therewith. The passage can be in fluid communication with an exterior of the catheter.

51 Claims, 12 Drawing Sheets

U.S. PATENT DOCUMENTS

| | | | |
|---|---|---|---|
| 5,217,482 A | 6/1993 | Keith | |
| 5,221,270 A | 6/1993 | Parker | |
| 5,226,888 A | 7/1993 | Arney | |
| 5,252,159 A | 10/1993 | Arney | |
| 5,261,879 A | 11/1993 | Brill | |
| 5,267,958 A | 12/1993 | Buchbinder et al. | |
| 5,304,198 A * | 4/1994 | Samson | 606/194 |
| 5,328,468 A | 7/1994 | Kaneko et al. | |
| 5,334,147 A | 8/1994 | Johnson | |
| 5,357,978 A | 10/1994 | Turk | |
| 5,370,615 A | 12/1994 | Johnson | |
| 5,395,334 A | 3/1995 | Keith et al. | |
| 5,410,797 A * | 5/1995 | Steinke et al. | 29/435 |
| 5,413,557 A | 5/1995 | Solar | |
| 5,413,560 A | 5/1995 | Solar | |
| 5,425,711 A | 6/1995 | Ressemann et al. | |
| 5,460,185 A | 10/1995 | Johnson et al. | |
| 5,470,315 A | 11/1995 | Adams | |
| 5,480,383 A | 1/1996 | Bagaoisan et al. | |
| 5,496,346 A | 3/1996 | Horzewski et al. | |
| 5,500,180 A | 3/1996 | Anderson et al. | |
| 5,538,510 A | 7/1996 | Fontirroche et al. | |
| 5,545,138 A | 8/1996 | Fugoso et al. | |
| 5,549,553 A | 8/1996 | Ressemann et al. | |
| 5,549,563 A | 8/1996 | Kronner et al. | |
| 5,605,543 A | 2/1997 | Swanson | |
| 5,634,902 A | 6/1997 | Johnson et al. | |
| 5,649,909 A | 7/1997 | Cornelius | |
| 5,658,251 A | 8/1997 | Ressemann et al. | |
| 5,667,493 A | 9/1997 | Janacek | |
| 5,669,932 A | 9/1997 | Fischell et al. | |
| 5,702,439 A | 12/1997 | Keith et al. | |
| 5,728,067 A | 3/1998 | Enger | |
| 5,738,667 A | 4/1998 | Solar | |
| 5,755,685 A | 5/1998 | Andersen | 604/53 |
| 5,775,685 A | 7/1998 | Yamaoka et al. | |
| 5,807,355 A | 9/1998 | Ramzipoor et al. | |
| 5,820,594 A | 10/1998 | Fontirroche et al. | |
| 5,824,173 A | 10/1998 | Fontirroche et al. | |
| 5,836,965 A | 11/1998 | Jendersee et al. | |
| 5,843,032 A | 12/1998 | Kastenhofer | |
| 5,851,464 A | 12/1998 | Davila et al. | |
| 5,891,056 A | 4/1999 | Ramzipoor | |
| 5,891,110 A | 4/1999 | Larson et al. | |
| 5,902,290 A | 5/1999 | Peacock, III et al. | |
| 5,980,486 A | 11/1999 | Enger | |
| 6,004,291 A | 12/1999 | Ressemann et al. | |
| 6,010,521 A | 1/2000 | Lee et al. | |
| 6,017,323 A | 1/2000 | Chee | |
| 6,027,477 A | 2/2000 | Kastenhofer | |
| 6,030,405 A | 2/2000 | Zarbatany et al. | |
| 6,036,670 A | 3/2000 | Wijeratne et al. | |
| 6,036,715 A | 3/2000 | Yock | |
| 6,059,770 A | 5/2000 | Peacock, III et al. | |
| 6,071,273 A | 6/2000 | Euteneuer et al. | |
| 6,102,890 A | 8/2000 | Stivland et al. | |
| 6,123,698 A | 9/2000 | Spears et al. | |
| 6,129,708 A | 10/2000 | Enger | |
| 6,159,229 A | 12/2000 | Jendersee et al. | |
| 6,165,166 A | 12/2000 | Samuelson et al. | |
| 6,187,130 B1 | 2/2001 | Berard et al. | |
| 6,193,686 B1 | 2/2001 | Estrada et al. | |
| 6,210,364 B1 | 4/2001 | Anderson et al. | |
| 6,254,549 B1 * | 7/2001 | Ramzipoor | 600/585 |
| 6,273,874 B1 | 8/2001 | Parris | |
| 6,283,939 B1 | 9/2001 | Anderson et al. | |
| 6,306,124 B1 | 10/2001 | Jones et al. | |
| 6,309,402 B1 | 10/2001 | Jendersee et al. | |
| 6,344,029 B1 | 2/2002 | Estrada et al. | |
| 6,361,529 B1 | 3/2002 | Goodin et al. | |
| 6,368,302 B1 | 4/2002 | Fitzmaurice et al. | |
| 6,402,720 B1 | 6/2002 | Miller et al. | |
| 6,475,209 B1 | 11/2002 | Larson et al. | |
| 6,488,694 B1 | 12/2002 | Lau et al. | |
| 6,527,789 B1 | 3/2003 | Lau et al. | |
| 6,530,938 B1 | 3/2003 | Lee et al. | |
| 6,565,588 B1 * | 5/2003 | Clement et al. | 606/180 |
| 6,575,958 B1 | 6/2003 | Happ et al. | |
| 6,575,993 B1 | 6/2003 | Yock | |
| 6,633,648 B1 | 10/2003 | Bauck | |
| 6,648,854 B1 | 11/2003 | Patterson et al. | |
| 6,652,507 B2 | 11/2003 | Pepin | |
| 6,663,648 B1 | 12/2003 | Trotta | 606/194 |
| 6,685,720 B1 | 2/2004 | Wu et al. | |
| 6,692,460 B1 | 2/2004 | Jayaraman | |
| 6,695,812 B2 | 2/2004 | Estrada et al. | |
| 6,702,750 B2 | 3/2004 | Yock | |
| 6,733,473 B1 | 5/2004 | Reifart et al. | |
| 6,733,487 B2 | 5/2004 | Keith et al. | |
| 6,814,744 B2 | 11/2004 | Yang et al. | |
| 6,821,281 B2 | 11/2004 | Sherman et al. | |
| 6,821,287 B1 | 11/2004 | Jang | 606/194 |
| 6,887,219 B2 | 5/2005 | Wantink | |
| 6,979,342 B2 | 12/2005 | Lee et al. | |
| 7,001,358 B2 | 2/2006 | Fitzmaurice et al. | |
| 7,025,258 B2 | 4/2006 | Chang | |
| 7,037,291 B2 | 5/2006 | Lee et al. | |
| 7,118,551 B1 | 10/2006 | Lee et al. | |
| 2001/0034514 A1 | 10/2001 | Parker | |
| 2002/0007146 A1 * | 1/2002 | Omaleki et al. | 604/103.09 |
| 2003/0105427 A1 | 6/2003 | Lee et al. | 604/103.04 |
| 2004/0010243 A1 | 1/2004 | Klint | |
| 2004/0236367 A1 | 11/2004 | Brown et al. | |

FOREIGN PATENT DOCUMENTS

| | | |
|---|---|---|
| EP | 0 029 185 A | 5/1981 |
| EP | 0518205 A | 12/1992 |
| EP | 0 806 220 A | 11/1997 |
| WO | WO/92/17236 | 10/1992 |
| WO | WO/2005/118044 | 5/2005 |
| WO | WO/2005/118045 | 5/2005 |
| WO | WO/2006/104591 | 2/2006 |

* cited by examiner

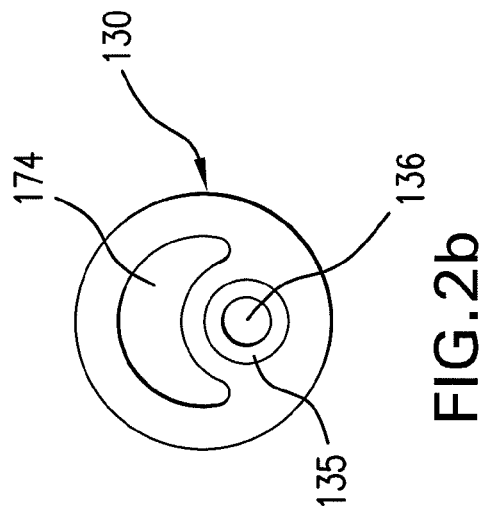
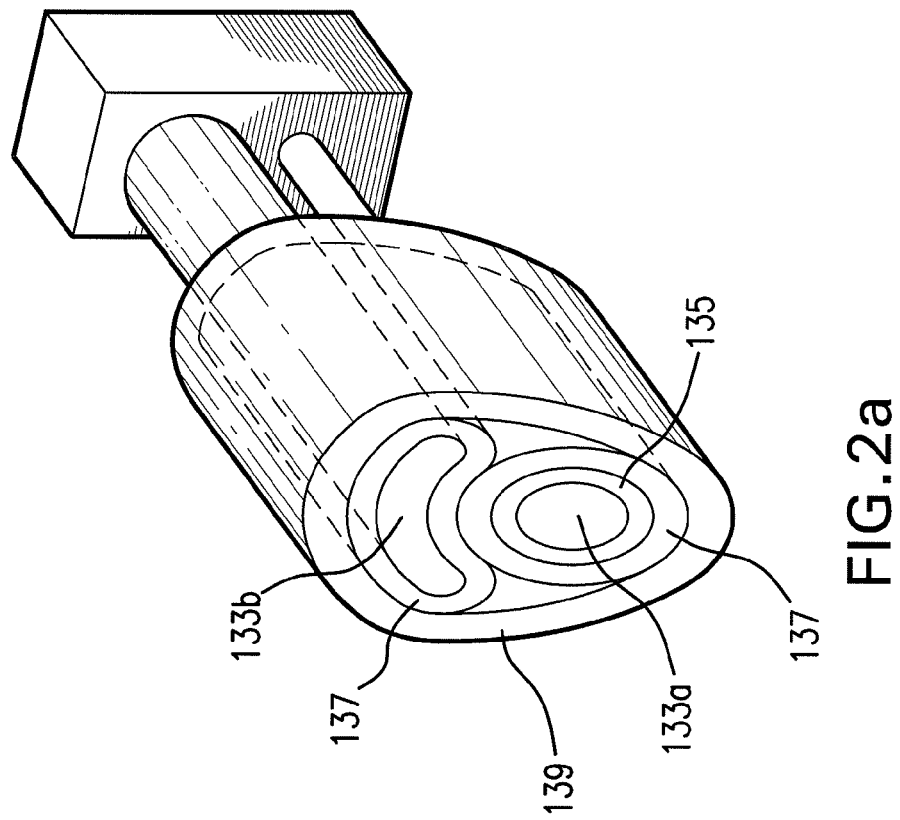

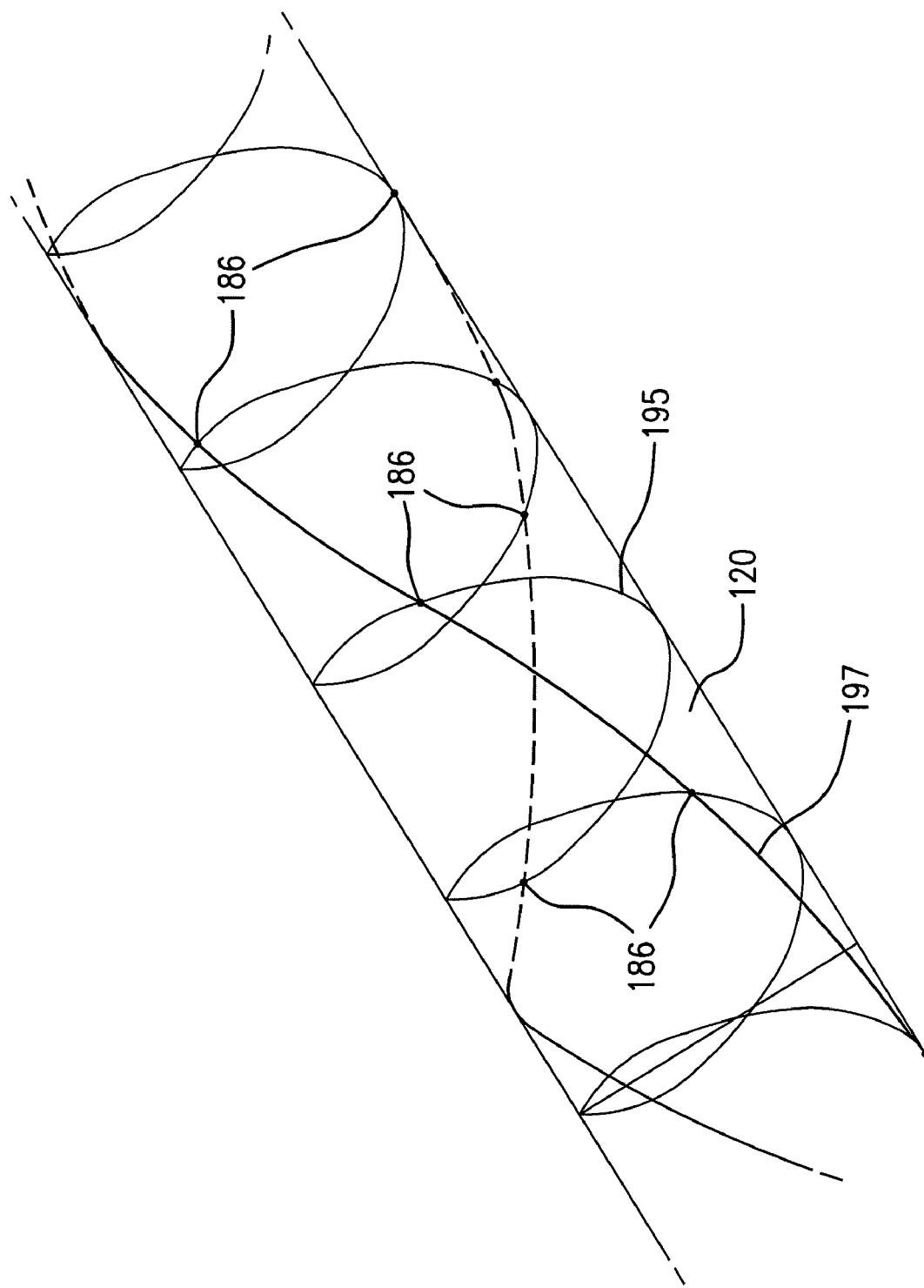

CATHETER HAVING MAIN BODY PORTION WITH COIL-DEFINED GUIDEWIRE PASSAGE

CROSS-REFERENCE

The present application claims the benefit of U.S. Provisional Patent Application Ser. No. 60/575,643 filed on May 27, 2004, the entire contents of which are incorporated herein by reference.

BACKGROUND OF THE INVENTION

1. Field of the Invention

The present invention relates to a catheter for treating a luminal system of a patient. Particularly, the present invention is directed to a catheter having a main body portion with a coil-defined guidewire passage. Moreover, the present invention provides an improved rapid exchange type catheter.

2. Description of Related Art

A variety of catheter devices are known in the art for treating the luminal system of a patient. Of such devices, many are directed to treating the cardiovascular system of a patient.

"Over the wire" catheters are generally known in the art. These devices are generally introduced into a patient after a guidewire has been introduced into the patient, and advanced to a treatment site within a patient where a treatment procedure (e.g., angioplasty and/or stent placement) is to be performed. The catheter is advanced over the guidewire to the treatment site, the treatment procedure is performed, and the catheter and guidewire are subsequently removed. Such systems can be disadvantageous. Because the guidewire lumen of an over the wire catheter must traverse the entire length of the catheter (which can exceed about 150 cm), either an extremely long guidewire (greater than 300 cm in length) or a guidewire extension must be used to permit the physician to maintain a grip on the guidewire and catheter during the treatment procedure.

To address this problem, rapid exchange catheters have been developed. Generally, a rapid exchange catheter has a relatively short guidewire lumen (e.g., less than 25 cm) near the distal end of the catheter, thus permitting the physician to use a standard length guidewire (e.g., 185-190 cm) to introduce a catheter and/or perform a catheter exchange.

Such conventional methods and systems generally have been considered satisfactory for their intended purpose. However, rapid exchange catheters still suffer from certain performance issues, such as a lack of pushability and kink resistance. Although solutions to this problem have been developed, such as by introducing metallic components (such as hypotubes) along the length of a catheter not supported by a guidewire, there still remains a continued need in the art for a catheter having enhanced pushability, kink resistance and versatility. The present invention provides a solution for these problems.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a catheter having an elongate main body portion and a distal body portion. The elongate main body portion has a proximal end and a distal end. The main body portion further includes a coil having at least one complete turn about a central axis, the coil defining a passage along the central axis. The elongate distal body portion extends from the distal end of the main body portion.

In accordance with still a further aspect of the invention, the coil can traverse substantially the entire length of the main body portion. Furthermore, the main body portion can include a proximal main body segment and a distal main body segment, wherein the coil traverses the length of the distal main body segment. The proximal main body segment can have a proximal end and a distal end, the distal end of the proximal main body segment being attached to the coil. The proximal main body segment can define a guidewire lumen in fluid communication with the passage defined by the turns of the coil.

In accordance with yet another aspect of the invention, the coil includes a plurality of turns, each turn having a length extending about the central axis, wherein at least one turn can be attached at an attachment location along its length to an adjacent turn. Moreover, each of a plurality of turns can be attached along its length to a respective adjacent turn at an attachment location.

In accordance with another aspect of the invention, the catheter can further comprise a flexible member disposed along a length of the coil. The flexible member can be attached to at least one turn of the coil and woven between selected remaining turns along the length of the coil.

In accordance with still another aspect of the invention, at least one turn of the coil can be spaced along its length from an immediately adjacent turn by a spacing, the spacing defining an intermediate opening in fluid communication with the passage.

In accordance with a further aspect of the invention, the stiffness of the main body portion can vary along its length. The variation can occur over the entire length of the main body portion, or a portion thereof. If a proximal main body segment is provided, the stiffness variation can occur along the length of the main body portion traversed by the coil. In accordance with this aspect of the invention, the stiffness of the catheter can be varied by varying spacing between adjacent turns of the coil, by varying the hardness of the coil, or by varying the dimensions of the coil, including but not limited to its wall thickness.

In accordance with a further aspect of the invention, the catheter can further include an elongate guide member having a guidewire capture structure at a distal end thereof. The guide member can be disposed for sliding movement within the guidewire lumen of the distal body portion and the passage defined by the coil. The guidewire capture structure can be a socket configured to engage the proximal end of a guidewire.

In accordance with a further aspect of the invention, the distal body portion has a proximal end and a distal end and can include a guidewire lumen defined along at least a portion of a length between the distal end and the proximal end of the distal body portion. The guidewire lumen has a distal guidewire port and a proximal guidewire port defined in communication therewith. The passage can be in fluid communication with an exterior of the catheter. The proximal guidewire port can also be aligned with the passage of the coil.

In accordance with another aspect of the invention, the distal body portion can further include an inflatable member.

In accordance with this aspect of the invention, an inflation lumen is defined along at least a length of the main body portion, wherein the inflation lumen is in fluid communication with the inflatable member. The main body portion can include a hollow tubular member configured into the at least one turn of the coil, the inflation lumen being defined within the hollow tubular member. Moreover, the inflation lumen can be further defined along at least a length of the main body portion. The hollow tubular member can extend along the at least a length of the main body portion with the inflation lumen defined therein. The hollow tubular member can be a single-piece hypotube.

In accordance with a further aspect of the invention, the distal body portion of the catheter can include a first distal body segment having the first guidewire lumen being defined therethrough, and a second distal body segment located proximal to the first distal body segment, the second distal body segment having a second guidewire lumen defined along at least a portion of a length thereof. The second guidewire lumen accordingly can be provided with a distal guidewire port and a proximal guidewire port in fluid communication therewith. The proximal guidewire port of the first guidewire lumen can be spaced distal to the distal guidewire port of the second guidewire lumen. The distal body portion can further include a distal transition region between the proximal end of the first distal body segment and the distal end of the second distal body segment.

The invention also includes a method of performing an medical procedure. The method includes providing a catheter as described herein, disposing a guidewire within a lumen of a patient, inserting the guidewire through the guidewire lumen of the distal end portion and at least a portion of the passage of the coil, and positioning the catheter along a length of the guidewire.

The method in accordance with the invention can include providing and inflating an inflatable member in a lumen of a patient, retracting the guidewire until a distal extremity of the guidewire is proximal to the proximal guidewire port of the distal end portion of the catheter, and allowing blood to perfuse through the guidewire lumen of the distal body portion. The method can also include providing an enlarged guidewire lumen to allow perfusion through the guidewire lumen of the distal body portion when the guidewire is positioned within the guidewire lumen.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 2(a) is a schematic view depicting the manufacture of a portion of the catheter of FIG. 1 in accordance with the present invention.

FIG. 2(b) is a cross sectional view of a portion of the catheter of FIG. 1 in accordance with the present invention.

FIG. 6 is an isometric schematic view depicting another aspect of a catheter in accordance with the present invention.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treating the luminal systems of a patient. The present invention is particularly suited for treatment of the cardiovascular system of a patient, such as performance of angioplasty and delivery of balloon-expandable or self-expanding interventional devices (e.g., stents, filters, coils).

In accordance with the invention, a catheter is provided having an elongate main body portion and a distal body portion. The elongate main body portion has a proximal end and a distal end. The main body portion further includes a coil having at least one complete turn about a central axis, the coil defining a passage along the central axis. The elongate distal body portion extends from the distal end of the main body portion.

Figure 1:
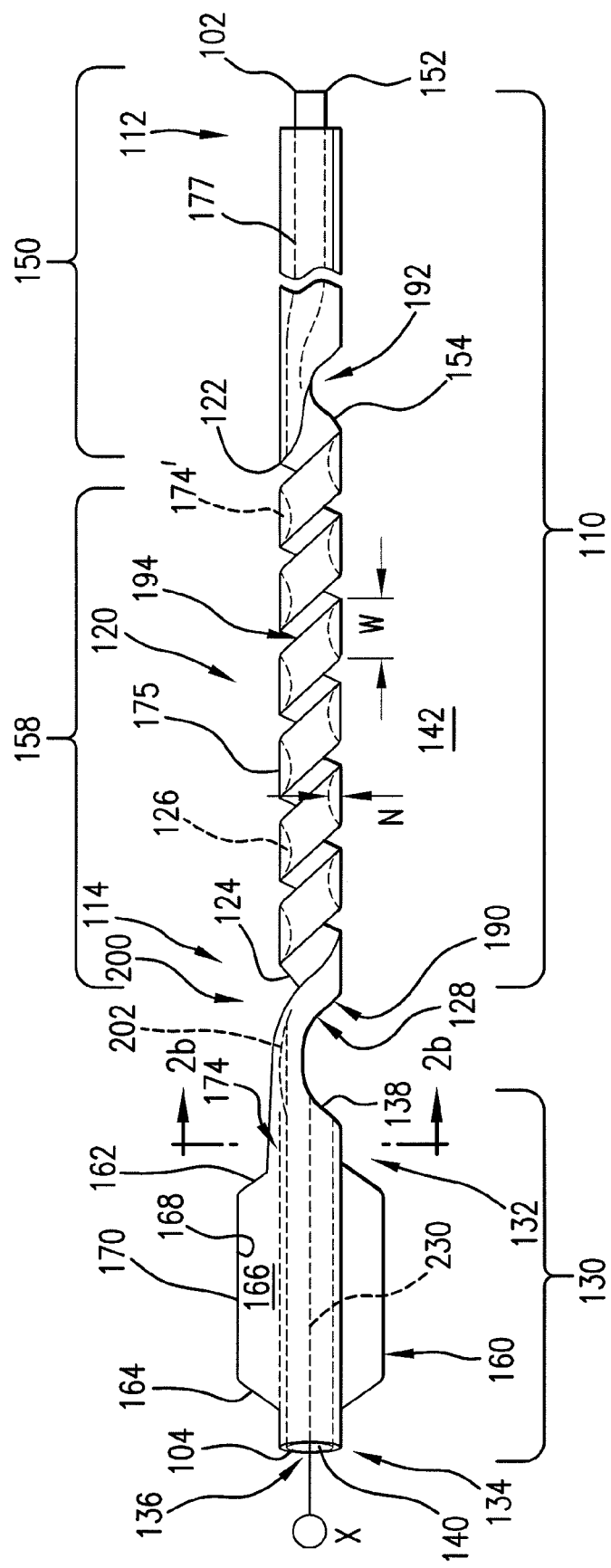
FIG. 1 is a partial side view of a first representative embodiment of a catheter having a main body portion with a coil-defined guidewire passage in accordance with the present invention.

For purpose of explanation and illustration, and not limitation, an exemplary embodiment of the catheter in accordance with the invention is shown in FIG. 1 and is designated generally by reference character 100. Other embodiments of a catheter in accordance with the invention, or aspects thereof, are provided in FIGS. 2-12, as will be described.

For purposes of illustration and not limitation, as embodied herein and as depicted in FIG. 1, catheter 100 has a proximal end 102 and a distal end 104. Distal body portion 130 has a proximal end 132, a distal end 134 and includes a guidewire lumen 136 defined along at least a portion of a length between the distal end 134 and the proximal end 132 of the distal body portion 130. The guidewire lumen 136 has a proximal guidewire port 138 and a distal guidewire port 140 defined in communication therewith. In a preferred embodiment, the proximal guidewire port 138 is aligned with passage 128 of coil 120. Preferably, each of the distal and proximal guidewire ports 140, 138, respectively is in communication with the exterior environment 142 of the distal end portion 130. Distal body portion 130 can also include one or more additional lumens, such as an inflation lumen 174, as discussed in detail below.

A variety of materials can be used for distal body portion 130. For example, distal body portion 130 can be made from any suitable polymer material such as polyamide, PEEK, PTFE, PVDF, Kynar, Kevlar, polyethylene of various suitable densities, polyester, polyurethane, or liquid crystal polymers. As a further exemplary alternative, distal body portion 130 can be a composite member comprising a fabrication of several different materials, such as reinforced polymer materials, including but not limited carbon, glass, or boron reinforced material, or an extrusion or pultrusion of different polymers, if desired. Alternatively, the composite member can be formed by a dip molding process, in which a mandrel is dipped into a polymer material, which has been dissolved in a suitable solvent, dried, and then re-dipped into another polymer material to form a multi-layered polymeric composite member. As yet another alternative, the composite member can be formed by applying a second polymeric tube about a first polymeric tube, applying a shrink tubing about first and second polymeric tube assembly and heating the assembly to fuse the first and second tubular members to each other. The composite member can also include a polymeric tubular member loaded with particles of a different polymer. For example and not limitation, a PEEK tubular member can be loaded with PTFE particles. In this manner, the PTFE particles can be electrostatically charged such that an electrostatic force bonds the PTFE particles to the PEEK tubular member. A polymeric outer layer, such as nylon tube, can be applied to the PTFE loaded tubular member to form a multi-material, multi-layer composite tubular member.

For purposes of illustration and not limitation, in order to fabricate distal body portion 130, polymer material can be formed about a mandrel 133a, 133b defining the guidewire lumen 136, and inflation lumen 174, if provided. Accordingly, a mandrel made of non-stick material, or alternatively a mandrel coated with a non-stick material, such as PTFE is preferred, such as that depicted in FIG. 2(a), having a shape corresponding to each lumen 136, 174, as desired. Preferably, a tubing segment 135 of lubricous material, such as high density polyethylene, PTFE or PVDF is placed over the portion 133a of the mandrel corresponding to the guidewire lumen. Plastic material 137, such as nylon (e.g., Nylon 12) in tubular form is fitted to the portion of the mandrel 133b corresponding to the inflation lumen and over tubing segment 135. The entire assembly is then placed inside a length of shrink wrap tubing 139 and heated. The application of sufficient heat will act to melt the nylon material, and cause the shrink wrap tubing to shrink and compress the molten plastic into a dual lumen distal body portion 130, a cross section of which being depicted in FIG. 2(b). Alternatively, distal body portion having guidewire lumen 136 and inflation lumen 174 can be fabricated by co-extrusion or other suitable alternate methods of manufacture, as known in the art.

A cross sectional view of distal body portion 130 as depicted in FIG. 2(b) demonstrates that guidewire lumen 136 has a substantially circular cross section to accommodate a guidewire, while inflation lumen 174 preferably has a crescent-shaped cross-section. Such a crescent-shaped cross section is advantageous because it maximizes the cross sectional area of inflation passage 174, thus minimizing flow resistance to inflate inflatable member 160.

In accordance with another aspect of the invention, the distal portion can include a device for performing an interventional procedure. For example, and for purposes of illustration and not limitation, as embodied herein and as depicted in FIG. 1, distal body portion 130 can further include an inflatable member 160 having a proximal end 162, a distal end 164, an interior chamber 166 bounded by a surface 168 of the inflatable member. Inflatable member 160 can be made from a variety of materials. For purpose of illustration and not limitation, inflatable member 160 can be made from a poly ether block amide ("PEBA"), nylon, polyhydroxyalkanoate, such as poly-4-hydroxybutyrate, distributed by Tepha Inc., Cambridge, Mass., or a variety of other materials. Inflatable member 160 can be attached to distal body portion 130 of catheter 100 by way of adhesive bond, fusion, or preferably by welding. Thus, if inflatable member 160 is made of nylon, it is advantageous for distal body portion 130 to be made of a material compatible for a welded bond therebetween.

Inflatable member 160 can be formed from a variety of methods. In accordance with one aspect of the invention, a coneless inflatable member made of suitable material is provided. In this manner, the inflatable member is formed from a thin walled tubular member having a proximal end and a distal end. The thin walled tubular member is placed about the distal body portion. Each of the proximal and distal ends of the thin walled tubular member is compressed onto the outer diameter of the distal body portion. In this manner, an Iris lens, a suture, a metal (with or without a non-stick coating) band, wire, or the like can be utilized to wrap around each of the proximal and distal ends of the thin tubular member and compress the proximal and distal ends onto the distal body portion.

Optionally, the thin walled tubular member can be folded before the compression step described above. For example and not limitation, the thin walled tubular member can include 2 to 10 folds. The proximal and distal ends of the thin walled tubular member can be secured to the distal body portion by a variety of suitable methods including adhesive, welding and fusion including but not limited to mechanical welding, laser welding, ultrasound welding, friction welding, heat welding, including light energy, RF energy, or any other suitable method known in the art.

Inflatable member 160 can be positioned on distal body portion 130 equidistant between the proximal end 132 and distal end 134 thereof. However, inflatable member 160 can also be placed closer to distal end 134 of catheter 100, if desired.

In accordance with a further aspect of the invention, the catheter can include a main body portion that includes a coil. The elongate main body portion 110 has a proximal end 112 and a distal end 114. The elongate distal body portion 130 extends from the distal end 114 of the main body portion 110. The main body portion 110 further includes a coil 120 having a proximal end 122, a distal end 124, and at least one complete turn 126 about a central axis X, such that the coil 120 defines a passage 128 along the central axis X. As defined herein, the term "central axis" refers to an imaginary line extending along and within the coil 120, and does not suggest that the imaginary line is located at a geometric center point of the coil cross section.

As depicted in FIG. 1, the coil preferably includes a number of turns. The passage 128 defined within the plurality of turns 126 of the coil 120 preferably is sized to accommodate a guidewire therethrough. The passage 128 can and preferably includes, a spacing 194 in fluid communication with an exterior 142 of the catheter 100. In this manner, and as will be described, a guidewire 230 can be inserted through the guidewire lumen 136 of the distal end portion 130, as with a conventional rapid exchange catheter, and (or alternatively) can be inserted through at least a portion of the passage 128.

The coil 120 thus retains the guidewire 230 against lateral displacement, which could damage or traumatize the vessel wall of the patient.

A variety of materials can be used for main body portion 110. Main body portion 110 is preferably formed of a suitable metallic material. Specifically, coil 120 is preferably formed from metal, such as various alloys of stainless steel or nitinol. If stainless steel is used, preferably austenitic stainless steel is used. Optionally coil 120 can be formed from a hardened material which is annealed to modify its flexibility. The use of a metallic material for main body portion 110 is particularly advantageous for rapid-exchange applications to enhance pushability. Main body portion 110 can also be formed of a suitable polymeric material such as PEEK or nylon, PTFE, PVDF, Kynar, Kevlar, polyethylene of various suitable densities, polyester, polyurethane, or liquid crystal polymers. As a further example, main body portion 110 can be formed of a composite member comprising a fabrication of several different materials, such as reinforced polymer materials, including carbon, glass, or boron reinforced material, or a co-extrusion or pultrusion of different polymers. The composite member can also be formed by the dip molding process, the process for fusing polymeric tubular members to each other, or the particle loading process, discussed above.

Figure 3:
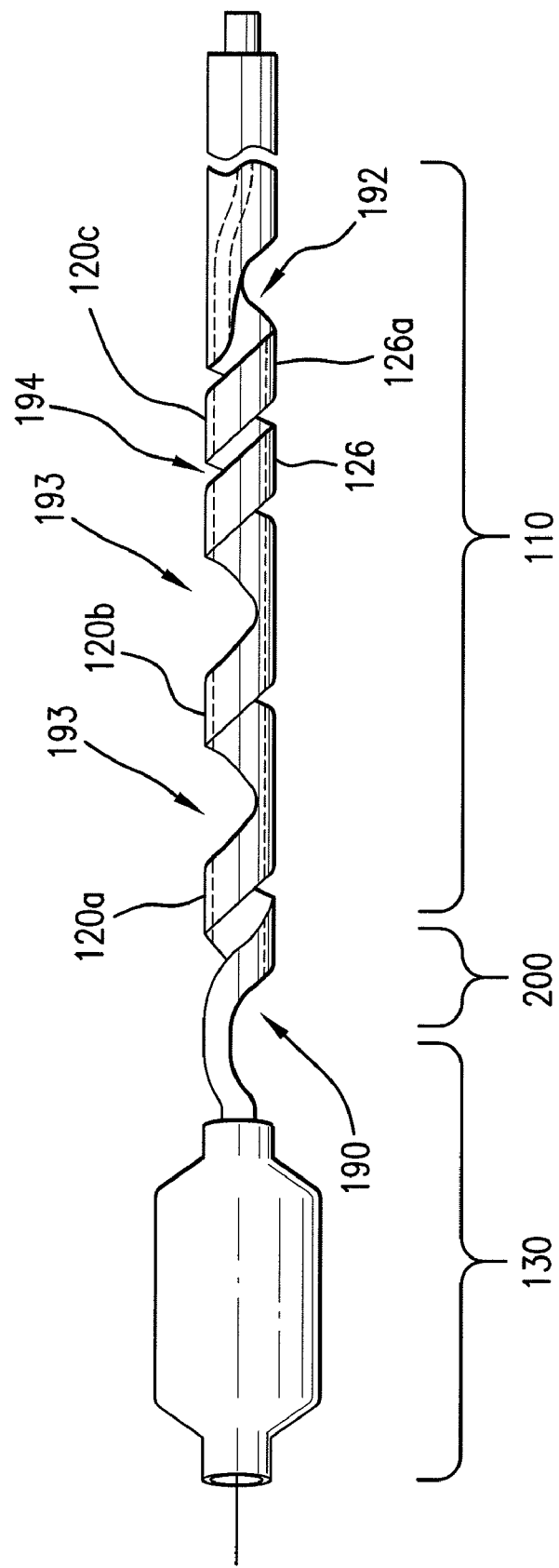
FIG. 3 is a partial side view of an alternative representative embodiment of a catheter in accordance with the present invention.

For purposes of illustration and not limitation, as embodied herein and as depicted in FIG. 3, the coil 120 can traverse substantially the entire length of the main body portion 110. Similarly, the coil 120 can be formed of a solid cross-section if no inflation lumen 174' is required. Preferably, as depicted in FIG. 1, main body portion 110 includes a proximal main body segment 150 and a distal main body segment 158, wherein the coil 120 traverses the length of the distal main body segment 158. As depicted herein, proximal main body segment 150 includes a proximal end 152 and a distal end 154, the distal end 154 of the proximal main body segment 150 being attached to the proximal end 122 of coil 120.

If provided, proximal main body segment 150 can be formed of a variety of different materials. Similar to distal body portion 130, proximal main body segment 150 can be formed of a polymeric material or composite material. The polymeric or composite proximal main body segment can further include a stiffening member, such as a metal filament, to modify its stiffness, if desired. Preferably, proximal main body segment 150 is formed at least in part of a metallic member, such as hypotube 177 (see FIG. 1). Such a construction provides catheter 100 with enhanced pushability and kink resistance. Moreover, a hypotube can act as a fluid conduit, or inflation lumen, if catheter 100 is provided with an inflatable member 160. Such a hypotube can be connected to, or integral with, hollow tubular member 175 forming coil 120.

In accordance with a further aspect of the invention, a variety of spacing configurations between turns of the coil can be used.

Figure 4:
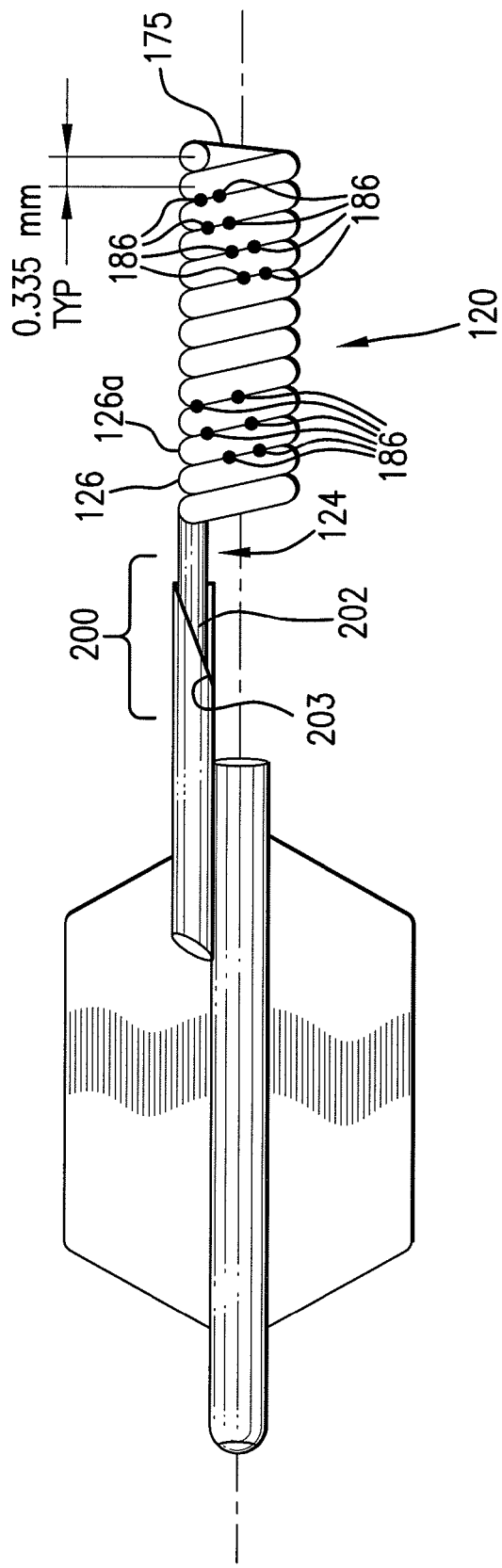
FIG. 4 is a partial side view of another alternative embodiment of a catheter in accordance with the present invention.
Figure 5B:
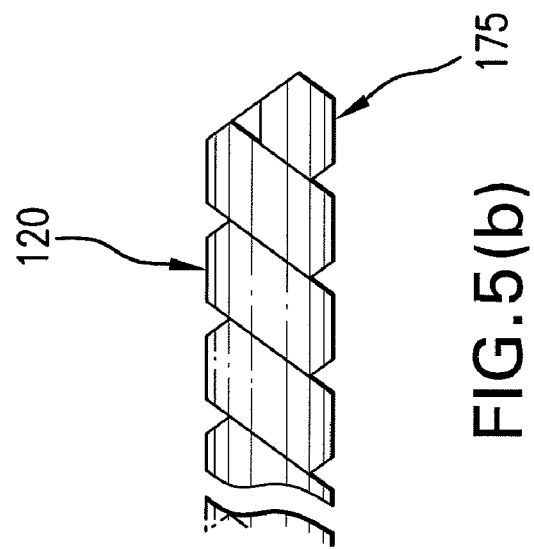
FIGS. 5(a)-5(b) are detail side views of alternative coil configurations for a catheter in accordance with the invention.
Figure 5A:
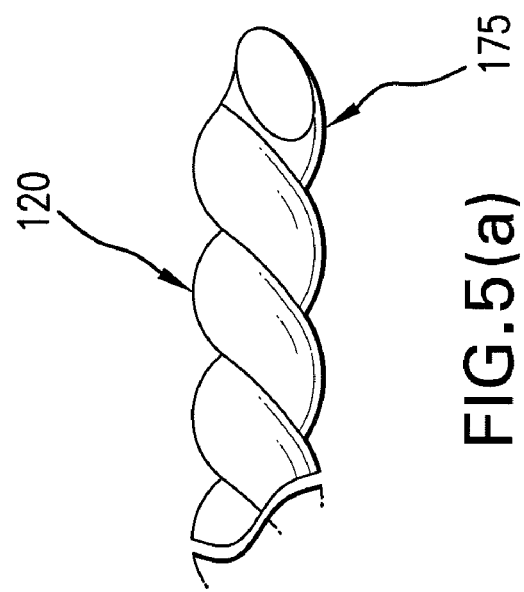

For purposes of illustration and not limitation, as embodied herein and as depicted in FIG. 4, each turn 126 of coil 120 can be substantially in contact along its length with an immediately adjacent turn, or can be slightly spaced from an adjacent turn as depicted in FIG. 1. A distal port 190 in fluid communication with the passage 128 thus can be defined at a distal end 124 of the coil 120, and a proximal port 192 in fluid communication with the passage 128 can be defined at a proximal end 122 of the coil 120.

Alternatively, and in accordance with another aspect of the invention, adjacent turns of the coil of the catheter can be separated by a spacing.

For purposes of illustration and not limitation, as embodied herein and as depicted in FIG. 3, coil 120 is provided with at least one turn 126 being spaced along its length from an immediately adjacent turn 126a by a spacing 194, the spacing 194 defining an intermediate opening in fluid communication with the passage. Spacing 194 can be provided along the length of coil 120. Port 190 can be located at the distal end 124 of coil 120. Port 190 can be positioned less than about 10 centimeters from the distal tip 104 of catheter 100.

In a similar manner, FIG. 3 can be construed to depict a plurality of coils 120a, 120b and 120c interconnected in series along a length of the main body portion 110. The plurality of coils 120a-120c can be interconnected in a spaced relationship to define elongate intermediate ports 193 between longitudinally-adjacent coils 120. Ports 190, 192, 193 are preferably between about 5 mm and 2 cm in length.

Figure 12:
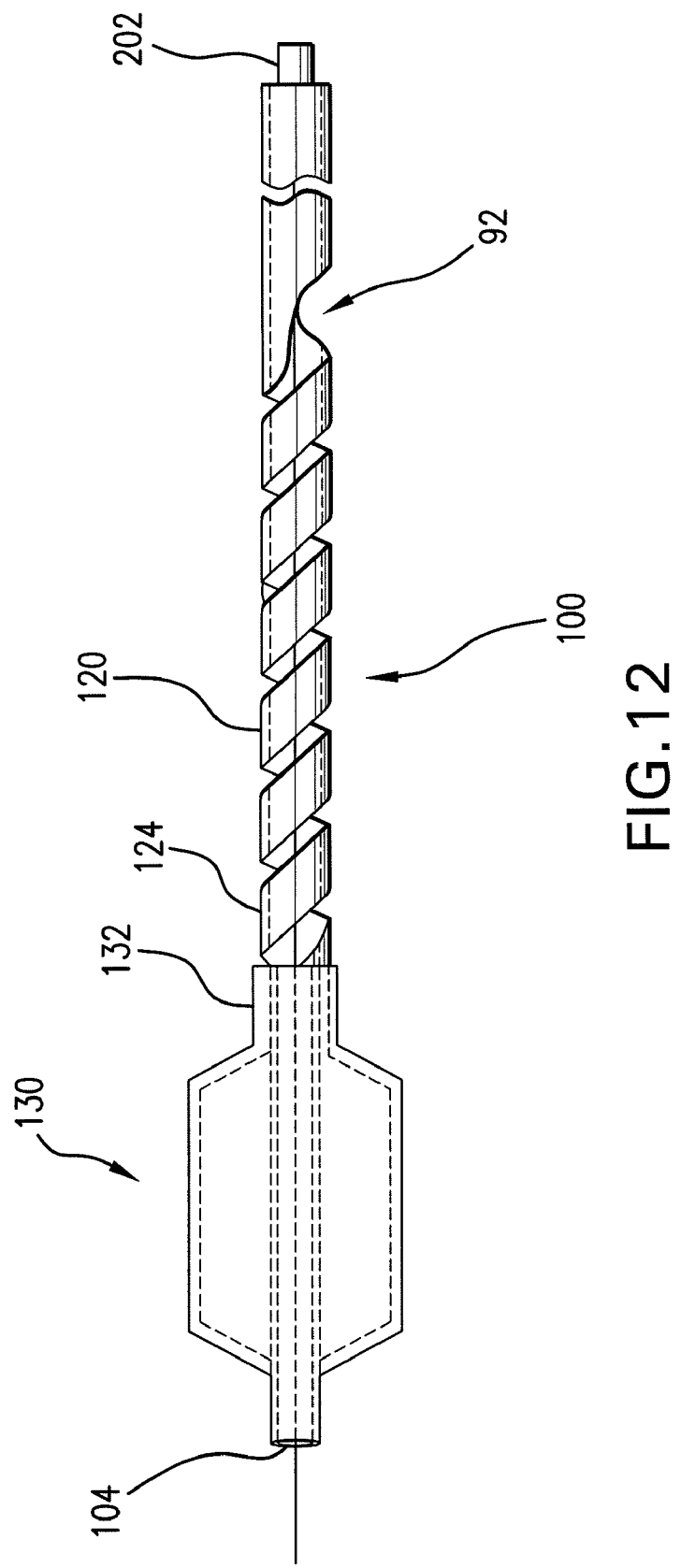
FIG. 12 is a partial cross-sectional side view of an additional embodiment of a catheter in accordance with the present invention.

By way of further example, and as depicted in FIG. 12, distal end 124 of coil 120 can be attached directly to the proximal end 132 of distal body portion 130, without an intervening transition section 200 and port 190. Such a device can further improve pushability of catheter 100 and prevent kinking.

As previously noted, an inflation lumen can be defined in the distal portion of the catheter if desired or necessary. Similarly, an inflation lumen can be defined through at least a portion of the main body portion. For example, and as depicted in FIG. 1, inflation lumen 174' is defined along at least a length of the main body portion 110, wherein the inflation lumen 174 is in fluid communication with inflation lumen 174, if provided, and the inflatable member 160 of the distal body portion 130.

In a preferred embodiment of the invention, the main body portion 110 is made of a hollow tubular member 175 configured into the at least one turn of the coil 120. The inflation lumen 174' is thus defined within the hollow tubular member 175. Moreover, the inflation lumen 174' can be further defined along at least a length of the main body portion 110. That is, and in a preferred embodiment of the invention, the hollow tubular member 175 extends along at least a length of and preferably along substantially the entire length of the main body portion 110 with the inflation lumen 174' defined therein. The hollow tubular member 175 preferably is a single-piece hypotube.

The construction of the inflation lumen can take on a variety of forms. As depicted herein, hollow tubular member 175 is formed into the coil 120, which can be connected to a hypotube 177 or like structure in main body portion 110. Hypotube 177 can be connected to coil 120 by way of laser welding or the like. In a preferred embodiment, however, the hollow tubular member is a single piece such as a hypotube, forming the coil and the hypotube of the proximal main body section 150 with an inflation lumen 174' defined therethrough.

Hollow tubular member 175 need not necessarily be a hypotube, but alternatively can be of composite construction or a braided shaft, such as a polymeric tube incorporating a metallic braid material. Such a braided tube can be made by sandwiching a braided layer between inner and outer polymeric layers, or can constitute a metallic reinforcing member impregnated with a polymer, such that it does not comprise two sandwiched polymeric layers. Alternatively, hollow tubular member 175 can be a polymeric construction including a stiffening member, such as a metal filament, disposed in the lumen of the hollow tubular member.

For purposes of illustration and not limitation, as embodied herein and as depicted in FIG. 4, the hollow tubular member 175 can have a substantially circular cross-sectional shape.

Alternatively, the hollow tubular member 175 can have a non-circular cross-sectional shape. For example, the non-circular cross-sectional shape of the hollow tubular member 175 can be substantially elliptical (FIG. 5(*a*)), substantially rectangular (FIG. 1), or be defined by a polygon (e.g., a hexagon) (FIG. 5(*b*)), among others.

An advantage of using a coil with a substantially rectangular cross section is that it can provide for a catheter with a relatively low profile (e.g., an overall diameter below 2.6F), while maximizing the cross sectional area of the flow passage to minimize resistance to the flow of inflation fluid to inflate inflatable member 160. By way of example, not for purposes of limitation, as depicted in FIG. 1, the cross section of coil 120 can have a narrow dimension N of about 0.33 mm and a width dimension W of about 1.2 mm. Any other suitable combination of dimensions is possible to accommodate the intended use of the catheter, and is well within the scope of the invention.

By way of further example, an inflation device (not shown) is provided for inflating the inflatable device 160. The inflation device can be, for example, a syringe or a flexible reservoir that is connected to proximal connector 152 (FIG. 1) and actuated by the physician to inflate the inflatable device 160.

Depending upon the materials of construction, and the intended use of the catheter, it may be beneficial to reinforce the coil. Hence, in further accordance with the invention, at least one turn of the coil can be attached at an attachment location along its length to an adjacent coil turn.

For purposes of illustration and not limitation, as embodied herein and as depicted in FIG. 4, at least one turn 126 of the coil 120 is attached at one or more attachment locations 186 along its length to an adjacent turn. The at least one turn 126 can be attached to the adjacent turn 126*a* by, for example, a spot weld or adhesive bond at attachment location 186. Moreover, each of a plurality of turns (or selected turns if desired) can be attached along its length to a respective adjacent turn at an attachment location 186.

In accordance with another aspect of the invention, successive attachment locations along a length of the coil can be circumferentially offset from each other. For example, FIG. 6 depicts a simplified schematic view of the coil 120 used in a catheter 100 in accordance with the invention, wherein reference number 195 is representative of the interface between adjacent turns of coil 120. In one preferred embodiment, successive attachment locations 186 between adjacent turns are arranged in a helical pattern 97 along the length of the coil 120, as depicted in FIG. 6. Generally, the pitch of the helical pattern will differ from or can be opposite to, the pitch of the coil. Such arrangement of the attachment locations 186 serve to provide lateral flexibility to the coil, while retaining its axial strength and inhibiting transverse displacement.

In a similar manner, and in accordance with a further aspect of the invention, the at least one turn of the coil 120 can be attached at a plurality of attachment locations 186 to the adjacent turn as depicted in FIG. 4. Moreover, each of a plurality of turns 126 can be attached along its length to a respective adjacent turn 126 at a plurality of attachment locations 186, where successive attachment locations 86 along a length of the coil are circumferentially offset from each other. As depicted in FIG. 6, successive attachment locations 186 can be arranged in a helical pattern along the length of the coil 120. For example, if two successive patterns are provided, each attachment location 186 is offset 180 degrees from the other. Likewise, if three successive patterns are provided, each attachment location 186 is offset 120 degrees from the other.

Alternatively, and in accordance with another aspect of the invention, the catheter can further comprise a flexible member disposed along a length of the coil. The flexible member is disposed to enhance the ability of the coil portion of the catheter to resist excessive longitudinal expansion, while retaining lateral flexibility.

Figure 7:
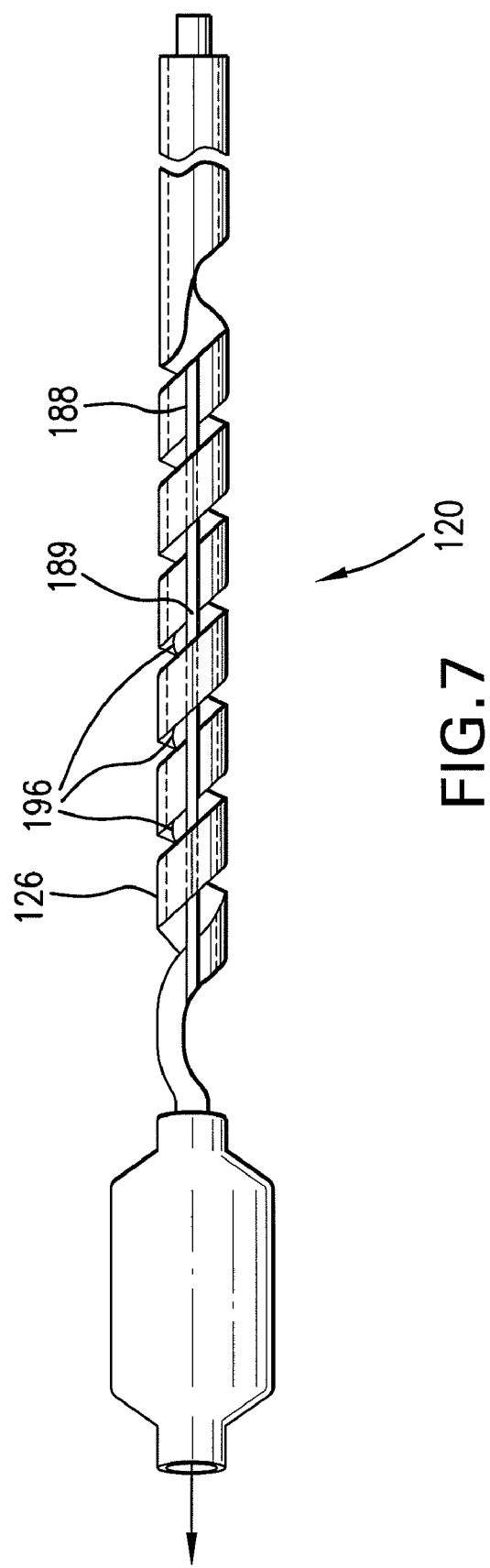
FIG. 7 is a partial side view of an alternative embodiment of a catheter in accordance with the present invention.

For purpose of illustration and not limitation, as embodied herein and as depicted in FIG. 7, flexible member 188 is disposed along a length of the coil 120. The flexible member 188 can be attached to at least one turn of the coil 120 and woven or wrapped between selected remaining turns along the length of the coil 120. For example, an endless belt can be wrapped around the turns within the selected length of coil 120, or the band can be woven in a criss-cross or a basket weave manner between adjacent turns. Moreover, the flexible member 188 can be attached to the coil 120 at a plurality of attachment locations 189 along a length of the coil 120, such as at opposing ends of the coil depicted in FIG. 7. Flexible member 88 need not be disposed along the entire length of coil 120.

Flexible member 188 is preferably provided in the form of a strand, such as a filament or web, of material having high axial strength, such as PTFE material. However, other materials are possible and within the scope of the invention. For example, a stainless steel or other similar metallic ribbon may be employed as flexible member 188. Advantageously, if a stainless steel ribbon is used in combination with a stainless steel coil 120, fusion between the two at one or more locations is more easily accomplished. If coil 120 is provided in polymeric form, or in metallic form with a suitable polymeric coating (e.g., PTFE-coated hypotube material), it is possible to weld a PTFE ribbon to the PTFE-coated hypotube. Alternatively, the flexible member can simply be tied to or wrapped around a turn 126 of the coil 120.

In accordance with a further aspect of the invention, the turns of the coil can define a first pitch, and the flexible member can be arranged on a helical path defining a second pitch different from the first pitch.

Figure 8:
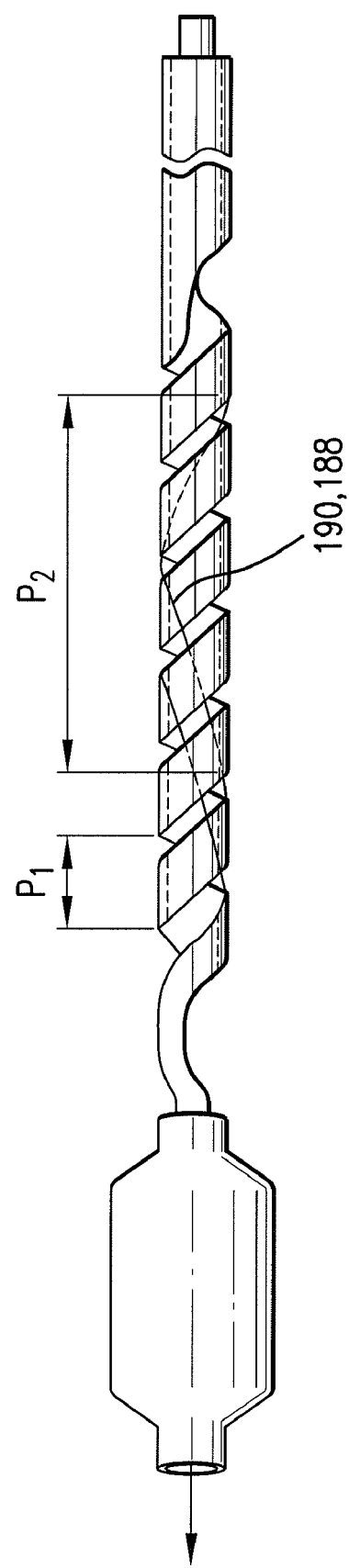
FIG. 8 is a partial side view of an additional alternative embodiment of a catheter in accordance with the present invention.

For purposes of illustration and not limitation, as depicted herein in FIG. 8, the turns of the coil 120 can define a first pitch P1, wherein the flexible member 188 is aligned on a helical path 190 defining a second pitch P2 along at least a portion of the length of the coil 120. The helical path 190 preferably has a pitch P2 that is different than the first pitch P1 of the coil 120. The flexible member 188 can be attached to the coil 120 by adhesive, or by fusion, depending on the selection of materials.

For purposes of illustration, and not limitation, the pitch between adjacent coil turns P1 can be about 0.335 mm, as depicted in FIG. 4. The pitch P2 of helical path is preferably longer as depicted in FIG. 8. Likewise, a reverse pitch can be used for the flexible member relative to the coil, if desired.

Moreover, coil 120 can be made from shape memory material, such as nitinol. Advantageously, if nitinol is used to construct coil 120, the coil can be trained to create a memory that causes the spacing 194 between adjacent coil turns 126 (i.e., the pitch) to increase as the catheter approaches body temperature. Accordingly, this permits for the coil turns 126 to be tightly spaced during introduction of the catheter, thereby providing excellent pushability, while creating a spacing between adjacent coil turns after insertion of catheter 100 into the luminal system of a patient, thereby facilitating perfusion of blood between spaced turns of the coil as described below in accordance with a method of the invention.

If coil 120 is provided in nitinol form and is conditioned to enlarge spacing 194 when inserted into a patient, flexible member 188 can be provided with some slack to permit elongation of coil 120. Thus, elongation of coil 120 can effectively be limited upon insertion into a patient. Additionally or alternatively, and as depicted in FIG. 7, collapsing nitinol strut members 196 can be arranged between adjacent turns 126 of the nitinol coil 120. These strut members 196 likewise can be trained to facilitate expansion of coil 120 after it is inserted into a patient. Where each pair of turns 126 is bridged by a strut 196, strut 196 can serve to prevent undesired elongation of coil 120 once it is fully expanded, similar to the function of flexible member 188.

In accordance with a further aspect of the invention, the stiffness of the main body portion can be varied along a portion of, or the entirety of its length. With reference to FIG. 1, the variation in stiffness can occur along the length of the coil 120, or the length of the entire main body portion 110, if desired. In accordance with this aspect of the invention, the stiffness of the catheter 100 can be varied by, among other things, varying spacing between adjacent turns 126 of the coil 120, by varying the hardness of the coil 120, or by varying the dimensions of the coil 120, including its wall thickness if coil 120 is provided in tubular form.

In accordance with a further aspect of the invention, the catheter can further include a transition region between the main body portion and the distal body portion. The purpose of the transition region, among other things, is to provide sufficient stiffness in an area of reduced cross-section of the catheter so as to prevent kinking.

For purposes of illustration and not limitation, as depicted in FIGS. 1 and 4, catheter 100 is provided with transition region 200 disposed between the distal end 114 of the main body portion 110 and the proximal end 132 of the distal body portion 130. The transition region 200 can include a reinforcement member 202. The reinforcement member 202 preferably includes a metallic member such as a filament, wire, coil, or braid. The reinforcement member 202 can alternatively include a ceramic composite material, or a carbon fiber reinforced material.

Alternatively, the reinforcement member can be provided in the form of a hypotube with a profile that diminishes in the distal direction of the catheter. For purposes of illustration and not limitation, as embodied herein and as depicted in FIG. 4, reinforcement member 202 is integrated with and a part of distal end 124 of coil 120. The profile of reinforcement member 202 is diminished in the form of a distally tapering segment of coil 120 that comes substantially to a point 203. Such a reduced profile helps facilitate a gradual change in stiffness along the length of the catheter 100 between coil 120, and comparatively flexible distal portion 130.

However, many other shapes and configurations are possible for reinforcement member 202 of the transition region 200. For example, reinforcement member 202 may take the form of a metallic filament fused to the distal end 124 of coil 120. The metallic filament can be straight and aligned along the central axis X of the catheter. Alternatively, a metallic element in the form of a coil can be provided, such as a helically-cut hypotube, attached to the distal end 124 of coil 120, or the transition can be provided by the coil itself if altered to provide a variation in stiffness. Accordingly, any suitable pattern can be formed in the distal end 124 of coil 120 to provide the desired transition in stiffness in transition region 200. Various patterns (helices, perforations, and the like) can be used, as long as the patterns can be formed by the machine being used to cut distal end 124 of coil 120. Moreover, since such laser cutters are typically used to cut stents, even a stent cell pattern could be formed into distal end 124 of coil 120. Transition regions to fulfill such a purpose are described, for example, in U.S. Pat. No. 6,273,879 to Keith, U.S. Pat. No. 5,743,876 to Swanson, U.S. Pat. No. 5,477,856 to Lundquist and U.S. Pat. No. 5,728,067 to Enger, each of which is explicitly incorporated by reference herein in its entirety.

In accordance with an additional aspect of the invention, the distal body portion can include a first distal body segment having the first guidewire lumen being defined therethrough and a second distal body segment located proximal to the first distal body segment. The second distal body segment can have a second guidewire lumen defined along at least a portion of a length thereof, the second guidewire lumen having a distal guidewire port and a proximal guidewire port defined in communication therewith. The proximal guidewire port of the first guidewire lumen can be spaced distal to the distal guidewire port of the second guidewire lumen. Each of the first and second guidewire lumen can include an inner surface having a lubricious coating.

Figure 9:
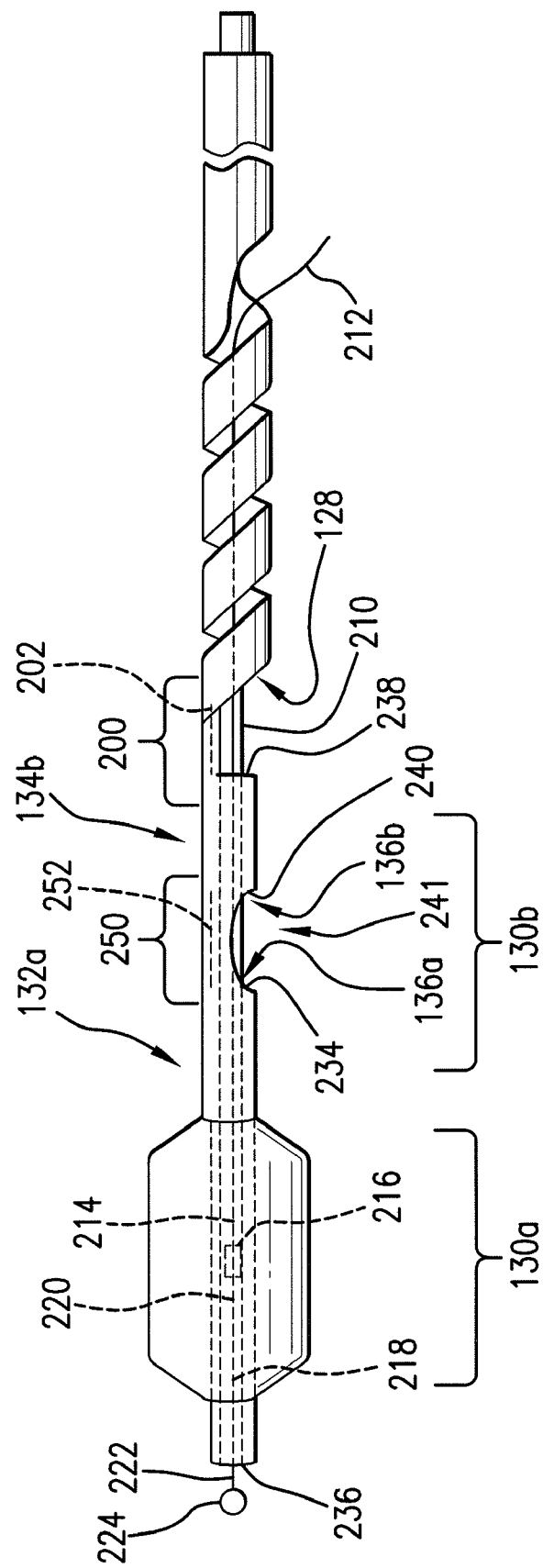
FIG. 9 is a partial side view of still another alternative embodiment of a catheter in accordance with the present invention.

For purposes of illustration and not limitation, and as depicted in FIG. 9, distal body portion 130 of catheter 100 includes a first distal body segment 130*a* having the first guidewire lumen 136*a* being defined therethrough, and a second distal body segment 130*b* located proximal to the first distal body segment 130*a*. The second distal body segment 130*b* has a second guidewire lumen 136*b* defined along at least a portion of a length thereof. The first guidewire lumen 136*a* accordingly can be provided with a proximal guidewire port 234 and a distal guidewire port 236 in fluid communication therewith. Similarly, the second guidewire lumen 136*b* accordingly can be provided with a proximal guidewire port 238 and a distal guidewire port 240 in fluid communication therewith. The proximal guidewire port 234 of the first guidewire lumen 136*a* can be spaced distally with respect to the distal guidewire port 240 of the second guidewire lumen 136*b* thus defining a port 241 between first guidewire lumen 136*a* and second guidewire lumen 136*b*.

The distal body portion 130 can further include a distal transition region 250 between a proximal end 132*a* of the first distal body segment 130*a* and a distal end 134*b* of the second distal body segment 130*b*. Although having a reduced cross section, distal transition region 250 is constructed with sufficient rigidity for preventing kinking, and, if desired, can provide for a transition in flexibility between distal portion 130*a* and distal portion 130*b*. For example, distal transition region can take the form of a fiber reinforced plastic material. Optionally, a metallic distal reinforcement member 252 can be provided in distal transition region 250.

Many shapes and configurations are possible for distal reinforcement member 252. For example, distal reinforcement member 252 can take the form of a metallic filament impregnated in a plastic matrix. Such a filament can be straight, or can take the form of a coil, or metallic tube having a stent-like structure, perforations, etc., as with reinforcement member 202. Moreover, reinforcement members 202, 252 can be provided in the form of ceramic materials, carbon fiber reinforced resin materials, and other such composite materials.

Further in accordance with the invention, an elongate guide member can be provided to facilitate passage of a guidewire through the various portions of the catheter. For purposes of illustration and not limitation, as embodied herein and as depicted in FIG. 9, a guide member 210 is provided having a proximal end 212, a distal end 214, and a guidewire capture structure 216 at distal end 214 thereof. For example, the guidewire capture structure can include a socket having an inside diameter greater than the outside diameter of the guidewire, a magnet, or any similar structure adapted to mate with a proximal end 232 of the guidewire 230. The length of the elongate guide member 210 is sufficient to extend at least a portion of the length of the catheter. The guide member 210 is disposed for sliding movement within the guidewire lumen 136 of the distal body portion 130 and/or the passage 128 defined by the coil 120, as desired.

Figure 10:
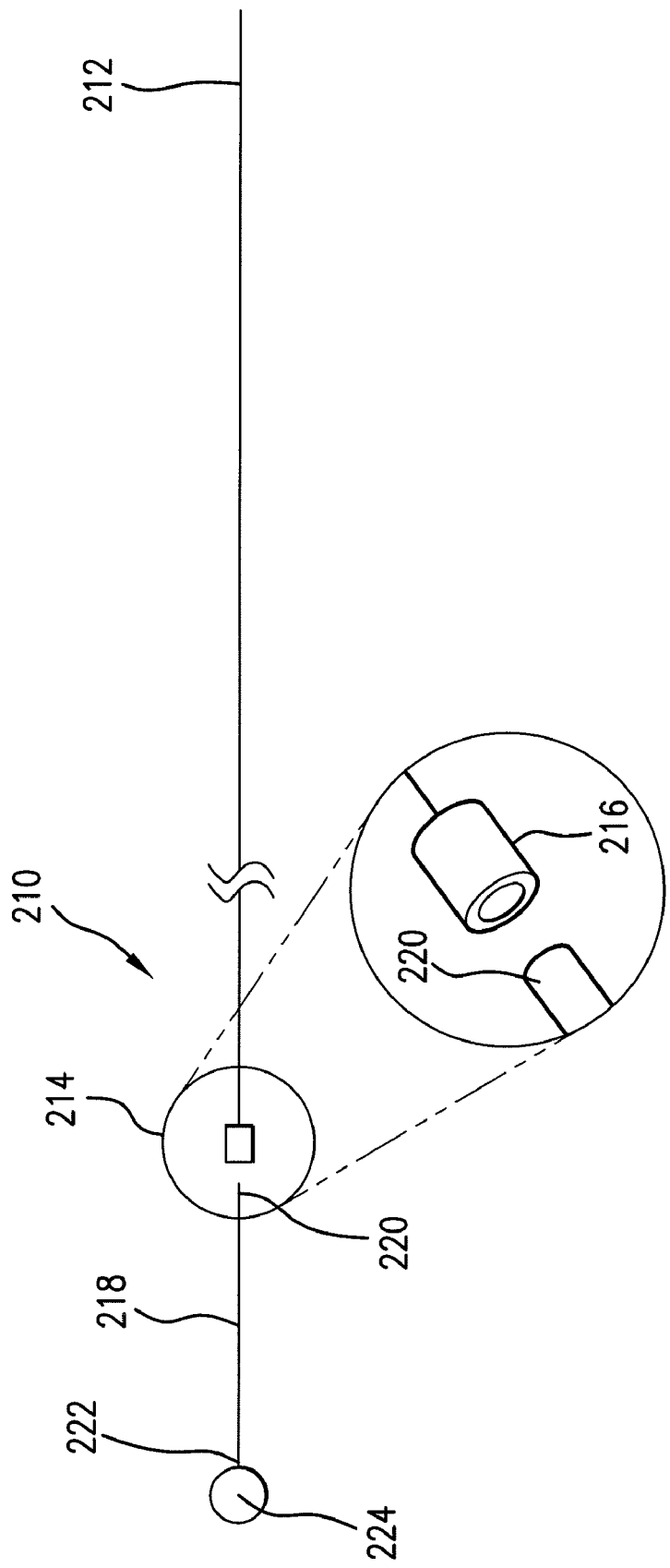
FIG. 10 is a schematic view of a capture device in accordance with the present invention.
Figure 11:
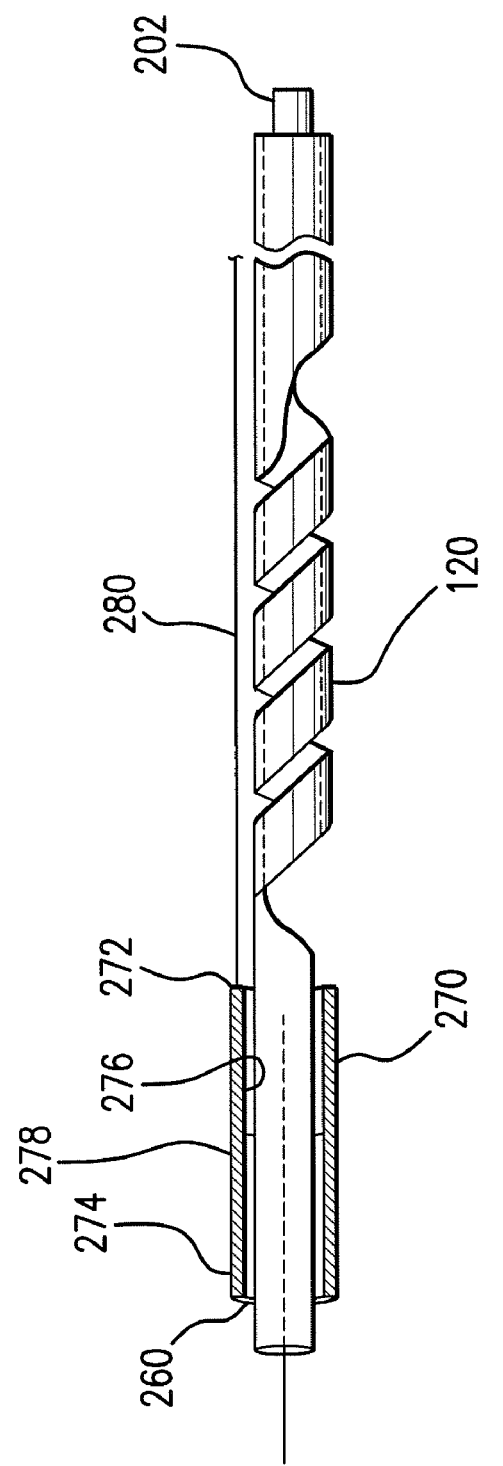
FIG. 11 is a partial cross-sectional side view of an additional alternative embodiment of a catheter in accordance with the present invention.

The guide member 210 can further include an elongate distal guide member portion 218 having a proximal end 220 configured to be engaged by the capture structure 216, and a distal end 222 having a handle 224, such as an eyelet or the like, to be gripped by a physician. The guidewire capture structure 216 can include a socket as depicted in FIG. 10 to engage the proximal end 232 of a guidewire 230 after guide member portion 218 is removed from capture structure 216.

In use, a physician first distally removes distal guide member portion 218, if provided, from catheter 100. The distal guide member portion 218 operates and performs a function similar to a conventional stylet used for shipment and preparation of the catheter. After any further necessary preparation (e.g., flushing and the like), catheter 100 is introduced over proximal end 232 of guidewire 230, wherein guidewire 230 already has been introduced in the patient and advanced to a treatment location. Proximal end 232 of guidewire 230 traverses a portion of guidewire lumen 236 until it engages guidewire capture structure 216. As guidewire 230 is further advanced proximally relative to catheter 100 (e.g., as catheter is advanced distally), guide member 210 effectively guides guidewire 230 through the remainder of guidewire lumen 136. The guide member 210 can be routed through catheter 100 so as to guide guidewire across any spacing 194, if provided, into passage 128 and out of port 190 or port 192 (see FIG. 1), or to bypass one or more portions, as desired. Guide member 210 thus facilitates use of catheter 100 for the physician.

A variety of structures can be used for guidewire capture structure 216. While a socket or cuff that receives or even frictionally engages proximal end 232 of guidewire 230 is depicted herein, it is also possible to provide other types of connections. For example, it is possible, although not necessary, to provide a latching mechanism that actively engages proximal end 232 of guidewire 230. Additionally or alternatively, if proximal end of guidewire 232 is provided with a coil (not shown), capture structure 216 can be provided with threads or teeth to mechanically interlock with guidewire 216, such that proximal end 212 of guide member of 210 can be gripped by a physician while gripping catheter 100 to facilitate movement of catheter 100 along guidewire 230.

A variety of types of medical devices are suitable for delivery by the delivery system of the present invention. For purpose of example and not limitation, a medical device can be provided, for example, in the form of a balloon-expandable stent (not shown). Such devices are generally well known in the art. However, the catheter 100 of the present invention is not limited to the delivery of balloon expandable stents. Other devices may also be used. For example, stent-grafts, coils, filters and embolic protection devices may be delivered within a patient's vasculature using catheter 100 of the present invention. Other devices such as a prosthesis retrieval mechanism or visual or ultrasonic imaging devices can also be delivered with catheter 100 to a predetermined location in a patient's luminal systems. Moreover, combinations of medical devices and/or beneficial agents can also be delivered using the device of the present invention. For example, multiple stents or a combination of stents and embolic protection devices and/or beneficial agents can be delivered using catheter 100 of the present invention, mounted on separate inflatable members (not shown).

Although reference has been made to a catheter having an inflatable member at its distal body portion, a variety of other structures for delivering to or use within a luminal system can be provided. For example, if desired, it is also possible to deliver self-expanding medical devices on catheter 100. In accordance with this aspect of the invention, a medical device in the form of a self-expanding prosthesis, such as a self-expanding stent 260, can be provided. If a self-expanding medical device 260 is to be delivered using catheter 100, it may be necessary to provide a restraint device 270 to restrain expansion of the medical device 260, and permit deployment at the appropriate time by a physician. Such a restraint device 270 can take the form of a retractable sheath 270 depicted in FIG. 11 having a proximal end 272, a distal end 274, an inner surface 276 and an outer surface 278. Sheath 270 can be withdrawn proximally so as to deploy the medical device 260 by actuating an actuator (not shown). The actuator can be a simple push-pull actuator, a gear mechanism, or a hydraulic actuator. The actuator can be attached to sheath 270 directly at proximal end 272 of sheath, or may be attached by a pull wire 280. Such actuators are provided in, for example, U.S. Pat. No. 6,425,898 to Wilson, U.S. Pat. No. 5,906,619 to Olson, U.S. Pat. No. 5,772,669 to Vrba and U.S. Pat. No. 6,527,789 to Lau et al., each of which is incorporated by reference herein in its entirety.

A variety of other restraint devices can additionally or alternatively be used. For example, restraint bands (not shown) could alternatively be used that are retracted proximally by a pull wire attached to an actuator. Similarly, restraint device 270 can take the form of a frangible envelope (not shown) with a pull wire embedded within the wall of the envelope. Self expanding medical device 260 can accordingly be deployed by actuating actuator, which pulls back on the pull wire, splitting open the frangible envelope, resulting in deployment of the self-expanding device. Other possible actuators (e.g., thermal actuation, wire restraints, balloon-ruptured restraints and the like) are also possible and within the scope of the invention.

In accordance with another aspect of the invention and as previously described in conjunction with certain aspects of the invention, a method of performing a medical procedure is provided. The method includes providing a catheter as described herein, disposing a guidewire within a lumen of a patient, inserting the guidewire through the guidewire lumen of the distal end portion and at least a portion of the passage of the coil, and positioning the catheter along a length of the guidewire. The catheter of the present invention can be used in the same manner as conventional rapid exchange catheters. Furthermore, if the coil 120 extends the entire length of the catheter, conventional over-the-wire methods can also be facilitated.

For purposes of illustration and not limitation, as embodied herein, the inserting step can include slidably disposing elongate guide member 210 having guidewire capture structure 216 at a distal end 214 thereof within the guidewire lumen 136 of the distal body portion 130 and the passage 128 of the coil 120. The method can further include receiving a proximal end 232 of a guidewire 230 in the guidewire capture structure 216 of guide member 210, and directing the guidewire 230 into the guidewire lumen 136 of the distal end portion 130 and at least a portion of the passage 128 of the coil 120 using the guide member 210.

The method in accordance with the invention can also include providing and inflating an inflatable member 160 in a lumen of a patient, retracting the guidewire 230 until a distal extremity of the guidewire is proximal to the proximal guidewire port 128 of the distal end portion 130 of the catheter, and allowing blood to perfuse through the guidewire lumen of the distal body portion.

In accordance with this aspect of the invention, if the adjacent turns 126 of the coil are spaced from one another as depicted in FIG. 1, turns 126 can define a helically shaped conduit or perfusion port, which can act as a perfusion path in fluid communication with distal guidewire lumen 136.

In further accordance with the method of the invention, the catheter provided in the providing step can include a distal body portion having a first distal body segment 130a having the first guidewire lumen 136a being defined therethrough, and a second distal body segment 130b located proximal to the first distal body segment 130a, the second distal body segment having a second guidewire lumen 136b defined along at least a portion of a length thereof, as depicted in FIG. 9. The inserting step can thus optionally include inserting the guidewire 230 through the first guidewire lumen 136a and the second guidewire lumen 136b of the distal end portion 130 and at least a portion of the passage 128 of the coil 120.

The methods and systems of the present invention, as described above and shown in the drawings, provide for a catheter with superior properties including superior flexibility and pushability. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A catheter comprising:
   an elongate main body portion having a proximal end and a distal end, the main body portion forming a coil having at least one complete turn about a central axis, the coil defining a passage along the central axis and at least one port in communication with the passage and an exterior of the catheter, the port being capable of receiving a guidewire therethrough; and
   an elongate distal body portion extending from the distal end of the main body portion, the distal body portion having a proximal end and a distal end, the distal body portion including a guidewire lumen defined along at least a portion of a length between the distal end and the proximal end of the distal body portion, the guidewire lumen having a distal guidewire port and a proximal guidewire port defined in communication therewith.

2. The catheter of claim 1, wherein the proximal guidewire port is aligned with the passage of the coil.

3. The catheter of claim 1 wherein the coil traverses substantially the entire length of the main body portion.

4. The catheter of claim 1, wherein the main body portion includes a proximal main body segment and a distal main body segment, wherein the coil traverses the length of the distal main body segment.

5. The catheter of claim 4, wherein the proximal main body segment has a proximal end and a distal end, the distal end of the proximal main body segment being attached to the coil.

6. The catheter of claim 5, wherein the proximal main body segment defines a guidewire lumen in fluid communication with the passage defined by the turns of the coil.

7. The catheter of claim 1, wherein the distal body portion further includes an inflatable member, and further wherein an inflation lumen is defined along at least a length of the main body portion, the inflation lumen in fluid communication with the inflatable member.

8. The catheter of claim 7, wherein the main body portion includes a hollow tubular member configured into the at least one turn of the coil, the inflation lumen being defined within the hollow tubular member.

9. The catheter of claim 8, wherein the inflation lumen is further defined along at least a length of the proximal main body segment.

10. The catheter of claim 9, wherein the hollow tubular member extends along the at least a length of the proximal main body segment with the inflation lumen defined therein, the hollow tubular member being a single-piece hypotube.

11. The catheter of claim 8, wherein the hollow tubular member has a substantially circular cross-sectional shape.

12. The catheter of claim 8, wherein the hollow tubular member has a non-circular cross-sectional shape.

13. The catheter of claim 12, wherein the non-circular cross-sectional shape of the hollow tubular member is substantially elliptical.

14. The catheter of claim 12, wherein the non-circular cross-sectional shape of the hollow tubular member is substantially rectangular.

15. The catheter of claim 12, wherein the non-circular cross-sectional shape of the hollow tubular member is defined by a polygon.

16. The catheter of claim 1, wherein the coil includes a plurality of turns, each turn having a length extending about the central axis, at least one turn attached at an attachment location along its length to an adjacent turn.

17. The catheter of claim 16, wherein the at least one turn is attached to the adjacent turn by a spot weld.

18. The catheter of claim 16, wherein each of a plurality of turns is attached along its length to a respective adjacent turn at an attachment location, successive attachment locations along a length of the coil being circumferentially offset from each other.

19. The catheter of claim 18, wherein successive attachment locations are arranged in a helical pattern along the length of the coil.

20. The catheter of claim 16, wherein the at least one turn is attached at a plurality of attachment locations to the adjacent turn.

21. The catheter of claim 20, wherein each of a plurality of turns is attached along its length to a respective adjacent turn at a plurality of attachment locations, successive attachment locations along a length of the coil being circumferentially offset from each other.

22. The catheter of claim 20, wherein successive attachment locations are arranged in a helical pattern along the length of the coil.

23. The catheter of claim 1, wherein the coil includes a plurality of turns, the catheter further comprising a flexible member disposed along a length of the coil.

24. The catheter of claim 23, wherein the flexible member is attached to at least one turn of the coil and woven between selected remaining turns along the length of the coil.

25. The catheter of claim 23, wherein the flexible member is a strand of PTFE material.

26. The catheter of claim 23, wherein the flexible member is attached to the coil at a plurality of attachment locations along a length of the coil.

27. The catheter of claim 26, wherein the turns of the coil define a first pitch, and further wherein the flexible member is aligned on a helical path along at least a portion of the length of the coil, the helical path having a pitch different than the first pitch of the coil.

28. The catheter of claim 26, wherein the flexible member is attached to the coil by adhesive.

29. The catheter of claim 26, wherein the flexible member is attached to the coil by fusion.

30. The catheter of claim 1, wherein the coil includes a plurality of turns, each turn having a length extending about the central axis, each turn substantially in contact along its length with an immediately adjacent turn.

31. The catheter of claim 1, wherein the at least one port defined by the coil is at an end of the coil.

32. The catheter of claim 1, wherein the at least one port defined by the coil is at an intermediate location along a length of the coil.

33. The catheter of claim 1, wherein the coil includes a plurality of turns, each turn having a length extending about the central axis, at least one turn being spaced along its length from an immediately adjacent turn by a spacing, the spacing defining an intermediate opening in fluid communication with the passage.

34. The catheter of claim 33, wherein the spacing between adjacent coil turns is substantially the same along the length of the coil.

35. The catheter of claim 1, wherein a plurality of coils are interconnected in series along a length of the main body portion.

36. The catheter of claim 35, wherein the plurality of coils are interconnected in a spaced relationship to define at least one intermediate port between longitudinally-adjacent coils.

37. The catheter of claim 1, wherein the stiffness of the main body portion varies along its length.

38. The catheter of claim 37, wherein the stiffness of the main body portion varies along the length of the main body portion traversed by the coil.

39. The catheter of claim 38, wherein the stiffness of the catheter is varied by varying spacing between adjacent turns of the coil.

40. The catheter of claim 38, wherein the stiffness of the catheter is varied by varying the hardness of the coil.

41. The catheter of claim 38, wherein the stiffness of the catheter is varied by varying the dimensions of the coil.

42. The catheter of claim 1 further comprising a transition region between the distal end of the main body portion and the proximal end of the distal body portion.

43. The catheter of claim 42, wherein the transition region includes a reinforcement member.

44. The catheter of claim 43, wherein the reinforcement member includes a metallic member selected from the group consisting of a filament, wire, coil, and braid.

45. The catheter of claim 43, wherein the reinforcement member includes a ceramic composite material.

46. The catheter of claim 43, wherein the reinforcement member includes a carbon fiber reinforced material.

47. The catheter of claim 1, further comprising an elongate guide member having a guidewire capture structure at a distal end thereof, the guide member being disposed for sliding movement within the guidewire lumen of the distal body portion and the passage of the coil.

48. The catheter of claim 47, wherein the guidewire capture structure is a socket configured to engage the proximal end of a guidewire.

49. The catheter of claim 48, wherein the guide member further includes an elongate distal guide member portion having a proximal end engaged with the socket, and distal end having a handle.

50. The catheter of claim 1, wherein the distal body portion includes:

a first distal body segment having the first guidewire lumen being defined therethrough; and a second distal body segment located proximal to the first distal body segment, the second distal body segment having a second guidewire lumen defined along at least a portion of a length thereof, the second guidewire lumen having a distal guidewire port and a proximal guidewire port defined in communication therewith, the proximal guidewire port of the first guidewire lumen being spaced distal to the distal guidewire port of the second guidewire lumen.

51. The catheter of claim 50, wherein the distal body portion further includes a distal transition region between the proximal end of the first distal body segment and the distal end of the second distal body segment.

* * * * *